US010579670B2

(12) United States Patent
Karavirta

(10) Patent No.: US 10,579,670 B2
(45) Date of Patent: Mar. 3, 2020

(54) PHYSIOLOGY-BASED SELECTION OF PERFORMANCE ENHANCING MUSIC

(71) Applicant: Polar Electro Oy, Kempele (FI)

(72) Inventor: Laura Karavirta, Jyvaskyla (FI)

(73) Assignee: Polar Electro Oy, Kempele (FI)

( * ) Notice: Subject to any disclaimer, the term of this patent is extended or adjusted under 35 U.S.C. 154(b) by 590 days.

(21) Appl. No.: 14/876,272

(22) Filed: Oct. 6, 2015

(65) Prior Publication Data
US 2017/0097994 A1 Apr. 6, 2017

(51) Int. Cl.
G06F 16/635 (2019.01)
G06F 16/23 (2019.01)
G06F 16/68 (2019.01)
A61B 5/0205 (2006.01)
G06Q 50/22 (2018.01)
G06Q 30/06 (2012.01)
A61B 5/024 (2006.01)
H04R 1/10 (2006.01)
A61B 5/00 (2006.01)
A61B 5/11 (2006.01)
G16H 40/67 (2018.01)
G16H 50/30 (2018.01)
G16H 20/30 (2018.01)
G16H 10/60 (2018.01)

(52) U.S. Cl.
CPC .......... G06F 16/636 (2019.01); A61B 5/024 (2013.01); A61B 5/0205 (2013.01); A61B 5/11 (2013.01); A61B 5/486 (2013.01); G06F 16/23 (2019.01); G06F 16/686 (2019.01); G06Q 30/0631 (2013.01); G06Q 50/22 (2013.01); G16H 10/60 (2018.01); G16H 20/30 (2018.01); G16H 40/67 (2018.01); G16H 50/30 (2018.01); H04R 1/1091 (2013.01); H04R 2499/11 (2013.01)

(58) Field of Classification Search
CPC .................................................. G06F 17/30764
See application file for complete search history.

(56) References Cited

U.S. PATENT DOCUMENTS

2007/0074619 A1* 4/2007 Vergo ....................... G10H 1/42
84/612
2007/0118043 A1* 5/2007 Oliver .................. A61B 5/0245
600/519

(Continued)

OTHER PUBLICATIONS

Karageorghis et al., "Music in the Exercise Domain: A Review and Synthesis (Part I)", International Review of Sport and Exercise Psychology, vol. 5, No. 1, pp. 44-66 (Mar. 2012).

(Continued)

Primary Examiner — Taelor Kim
Assistant Examiner — Dawaune A Conyers
(74) Attorney, Agent, or Firm — Fisherbroyles, LLP

(57) ABSTRACT

Physiology-based selection of performance enhancing music for a specific individual is disclosed. Internal effort data and external work data both measured from a user performing an exercise while listening to a specific music track are obtained. The internal effort data describes a measured bodily input of the user, and the external work data describes a measured output effect of the user. A comparison between the internal effort data and the external work data is performed. At least one performance enhancing music track for the user is selected based on the comparison.

19 Claims, 7 Drawing Sheets

(56) References Cited

U.S. PATENT DOCUMENTS

| | | | |
|---|---|---|---|
| 2007/0219059 A1* | 9/2007 | Schwartz | A61B 5/0205 |
| | | | 482/8 |
| 2007/0249467 A1 | 10/2007 | Hong et al. | |
| 2007/0287928 A1* | 12/2007 | Kiviniemi | A61B 5/02438 |
| | | | 600/508 |
| 2008/0176712 A1* | 7/2008 | Frimmer | A63B 71/0686 |
| | | | 482/3 |
| 2008/0188354 A1* | 8/2008 | Pauws | A63B 71/0686 |
| | | | 482/8 |
| 2011/0295843 A1* | 12/2011 | Ingrassia, Jr. | G06F 16/4387 |
| | | | 707/723 |
| 2014/0072128 A1 | 3/2014 | Ogg et al. | |
| 2015/0216427 A1 | 8/2015 | Granqvist et al. | |
| 2017/0289651 A1* | 10/2017 | Swanson | H04Q 9/00 |

OTHER PUBLICATIONS

Karageorghis et al., "Music in the Exercise Domain: A Review and Synthesis (Part II)", International Review of Sport and Exercise Psychology, vol. 5, No. 1, pp. 67-84 (Mar. 2012).
Yamasaki, et al., "The Impact of Music on Metabolism", Nutrition, vol. 28, pp. 1075-1080 (2012).
International Search Report, Application No. PCT/FI2016/050689, Ad van der Weiden (dated Feb. 12, 2016).

\* cited by examiner

PHYSIOLOGY-BASED SELECTION OF PERFORMANCE ENHANCING MUSIC

BACKGROUND

Field

The invention relates to an electronic apparatus, computer program and method in an electronic apparatus for selection of performance enhancing music.

Description of the Related Art

Music has both ergogenic (performance enhancing) and psychological (e.g. mood enhancing) effects during a physical exercise. The impact of a particular type of music or song depends on internal and external factors that are highly individual. A psychometric instrument has been developed in the scientific literature in order to rate the motivational qualities of music. However, this rating system involves manual work by the user. Therefore, there is a need to automatically identify user-specific music that produces the most favorable effects during the exercise.

SUMMARY

The present invention seeks to provide an improved electronic apparatus, computer program and method in an electronic apparatus for selection of performance enhancing music.

According to an aspect of the present invention, there is provided an electronic apparatus comprising: an interface; one or more processors; and one or more memories including computer program code, the one or more memories and the computer program code configured to, with the one or more processors, cause the apparatus at least to: obtain, with the interface, internal effort data and external work data both measured from a user performing an exercise while listening to a specific music track, the internal effort data describing a measured bodily input of the user, and the external work data describing a measured output effect of the user; perform a comparison between the internal effort data and the external work data; and select at least one performance enhancing music track for the user based on the comparison.

According to another aspect of the present invention, there is provided a non-transitory computer-readable storage medium comprising a computer program comprising computer program code which, when loaded into an electronic apparatus cause the apparatus at least to: obtain internal effort data and external work data both measured from a user performing an exercise while listening to a specific music track, the internal effort data describing a measured bodily input of the user, and the external work data describing a measured output effect of the user; perform a comparison between the internal effort data and the external work data; and select at least one performance enhancing music track for the user based on the comparison.

According to another aspect of the present invention, there is provided a method in an electronic apparatus, comprising: obtaining internal effort data and external work data both measured from a user performing an exercise while listening to a specific music track, the internal effort data describing a measured bodily input of the user, and the external work data describing a measured output effect of the user; performing a comparison between the internal effort data and the external work data; and selecting at least one performance enhancing music track for the user based on the comparison.

BRIEF DESCRIPTION OF THE DRAWINGS

Example embodiments of the present invention are described below, by way of example only, with reference to the accompanying drawings, in which.

DETAILED DESCRIPTION

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Figure 1:
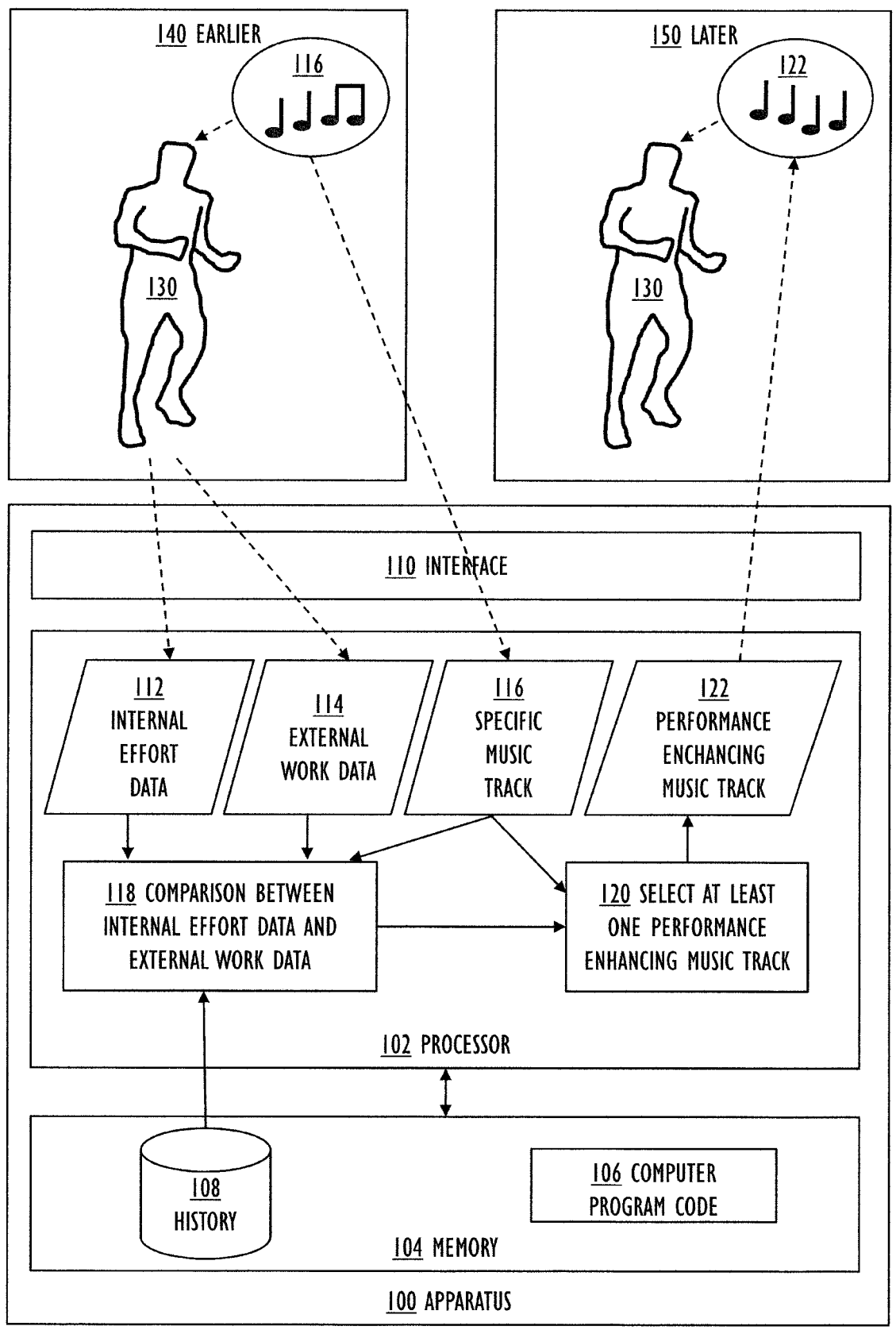
FIGS. 1, 2, 3, 4 and 5 illustrate example embodiments of an electronic apparatus.

FIG. 1 illustrates example embodiments of an electronic apparatus 100. It should be noted that while FIG. 1 illustrates various example embodiments of the apparatus 100, it is only a simplified block diagram that only shows some structures and functional entities. The connections shown in FIG. 1 are logical connections; the actual physical connections may be different. It is apparent to a person skilled in the art that the described apparatus 100 may also comprise other functions and structures. The same applies to FIGS. 2, 3, 4 and 5 as well. It should be appreciated that details of some functions, structures, and the protocols used for communication are irrelevant to the actual invention. Therefore, they need not be discussed in more detail here.

The apparatus 100 comprises an interface 110, one or more processors 102, and one or more memories 104 including computer program code 106.

The interface 110 is an electronic interface utilized to obtain various data, internally and/or externally.

The term 'processor' 102 refers to a device that is capable of processing data. Depending on the processing power needed, the apparatus 100 may comprise several processors 102 such as parallel processors or a multicore processor. When designing the implementation of the processor 102, a person skilled in the art will consider the requirements set for the size and power consumption of the apparatus 100, the necessary processing capacity, production costs, and production volumes, for example.

The term 'memory' 104 refers to a device that is capable of storing data run-time(=working memory) or permanently (=non-volatile memory). The working memory and the non-volatile memory may be implemented by a random-access memory (RAM), dynamic RAM (DRAM), static RAM (SRAM), a flash memory, a solid state disk (SSD), PROM (programmable read-only memory), a suitable semiconductor, or any other means of implementing an electrical computer memory.

The processor 102 and the memory 104 may be implemented by an electronic circuitry.

The computer program code 106 may be implemented by software and/or hardware.

In an example embodiment, the software may be written by a suitable programming language, and the resulting executable code 106 may be stored on the memory 104 and run by the processor 102.

In an example embodiment, the functionality of the hardware may be designed by a suitable hardware description language (such as Verilog or VHDL), and transformed into a gate-level netlist (describing standard cells and the electrical connections between them), and after further phases the chip implementing the processor 102, memory 104 and the code 106 of the apparatus 100 may be fabricated with photo masks describing the circuitry.

The one or more memories 104 and the computer program code 106 are configured to, with the one or more processors 102, cause the apparatus 100 at least to implemented the following three-phase sequence of operations:

1) Obtain, with the interface 110, internal effort data 112 and external work data 114 both measured from a user 130 performing an exercise while listening to a specific music track 116, the internal effort data 112 describing a measured bodily input of the user 130, and the external work data 114 describing a measured output effect of the user 130;
2) Perform a comparison 118 between the internal effort data 112 and the external work data 114; and
3) Select 120 at least one performance enhancing music track 122 for the user 130 based on the comparison 118.

Favorable effects of performance enhancing (motivational) music include, for example, faster self-selected pace with similar rating of perceived exertion (RPE), improved economy of locomotion, decreased heart rate and blood pressure, and improved mood. By systematically analyzing the physiological effects of particular song or type of music, the performance enhancing music may be identified and used individually for each user during training.

The following papers, incorporated herein by reference, explain in more detail the ways the music may enhance performance:

Alisa Yamasaki, Abigail Booker, Varun Kapur, Alexandra Tilt, Hanno Niess, Keith D. Lillemoe, Andrew L. Warshaw, Claudius Conrad: The impact of music on metabolism, Nutrition, Volume 28, Issue number 11-12, 2012; and Costas I. Karageorghis and David-Lee Priest: Music in the exercise domain, a review and synthesis (Parts I and II), International Review of Sport and Exercise Psychology, Vol. 5, No. 1, March 2012.

In an example embodiment, two different performance enhancing features of music may be distinguished:

1) Improved Economy of Locomotion During Submaximal Effort

Heart rate will be measured as the principle physiological parameter, and heart rate will be used together with pace, speed or power output data, to assess physical performance (aerobic capacity and economy). Music will be identified as motivational if it leads to improved economy.

2) Improved Performance During Maximal Effort

The maximal work output and/or maximal (peak) heart rate will be analyzed during sprint, high intensity interval or maximal strength training sessions when a certain song or certain type of music is played. If a song elicits higher performance than average the music will be identified as motivational.

In an example embodiment, music tracks that are identified as motivational in each category will be used more often during similar sessions whereas other music tracks are not played again or are not played as often. In an example embodiment, the impact of each music track may be updated each time it plays during exercise so that the motivational rating follows the changes in individual preferences over time.

The beneficial effects of music during exercise are twofold. Firstly, it will make the exercise more enjoyable by distracting attention from the pain or uncomfortableness of exercise, especially in untrained or less active individuals. Secondly, it will improve performance during training, thus leading to more effective training sessions and improved training benefits. It may also directly improve performance during a competition or race (if allowed).

In an example embodiment, performance enhancing music will be automatically selected for the user 130 for each training session so that the user 130 will get most out of each sessions and a more enjoyable training experience.

In an example embodiment, a sensor measures heart rate and another sensor detects external work (a stride sensor attached on the foot, GPS, or pedals for power measurement). A web based or offline music player may be used with an adequate selection of music. Headphones or other means of listening may be used. Physiological and physical measurement data will be analyzed in relation to each piece of music and in relation to the purpose (improved economy of locomotion during submaximal effort, or improved performance during maximal effort) and the resulting motivational index may be updated and stored locally or in an online source. The present coaching applications using music are quite basic at the moment and do not seem to use real time data analysis when selecting music. In the prior art, motivational qualities of music may be identified by self-selecting the preferred music during training. This is manual, time-consuming and only applies to the particular songs that are listed. The user may also manually rate each song based on his/her preference or rating of perceived exertion while the song is playing during exercise but this substantially disturbs the training session. Also, there may be individual physiological benefits of a certain type of music that the user is not conscious of.

In an example embodiment, in addition to being automatic from the user's point of view, the present example embodiments may be used during any music track that is played during exercise, not just the ones that have been rated before. Furthermore, it directly determines the physiological benefit of each music track by measuring physiological and physical parameters during exercise, and thus, does not solely rely on user's conscious choices.

FIG. 1 illustrates the temporal order of events: earlier 140, the user 130 listens to the specific the music track 116, and, later 150, the user 130 listens to the performance enhancing music track 122. The user 130 may listen to the music track 116, 122 with a loudspeaker, headphones, wireless headset, earbuds, or any other suitable equipment enabling the listening during the exercise.

In an example embodiment, the internal effort data 112 comprises at least one of a heart activity of the user 130, a breathing activity of the user 130, an energy consumption of the user 130, an electrodermal activity status 130 of the user 130, a stress of the user 130.

In an example embodiment, the external work data 114 comprises at least one of a speed of the user 130, a distance traveled by the user 130, a power outputted by the user 130, a pace of the user 130, an acceleration of the user 130, a peak work output by the user 130, an economy of motion status of the user 130, a running index of the user 130.

In an example embodiment, historical internal effort data 108 and historical external work data 108 from at least one earlier exercise session by the user 130 are taken into account in the comparison 118.

Figure 7:
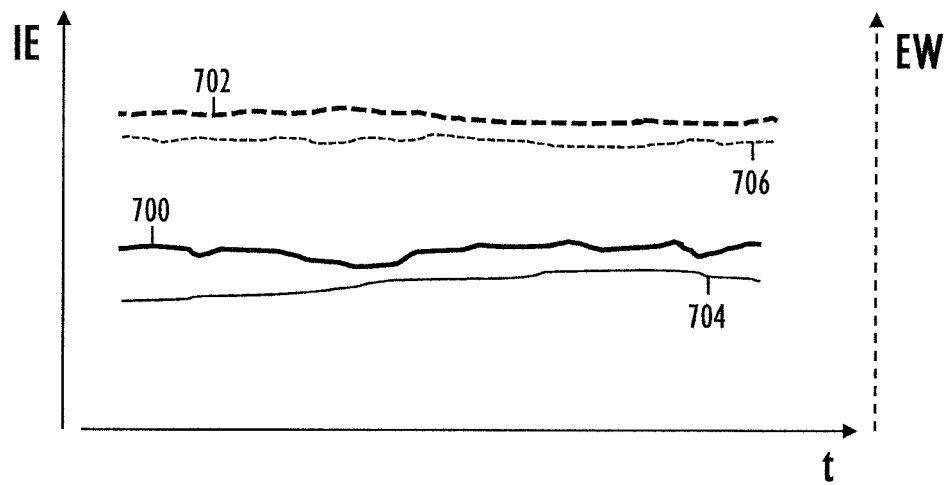
FIGS. 7, 8, 9 and 10 illustrate example embodiments of a comparison between internal effort data and external work data.

FIG. 7 illustrates a further example embodiment. The x axis illustrates the time, the y axis illustrates both the internal effort IE and the external work EW, and curves 700, 702, 704, 706 illustrate internal effort data as a function of time with solid lines and external work data with dotted lines.

In the example embodiment, the comparison 118 indicates that the specific music track 116 is performance enhancing provided that, as compared to the historical internal effort data 704 and the historical external work data 706, the internal effort data 700 indicates an increase in the measured bodily input of the user 130 and the external work data 702 indicates an increase in the measured output effect of the user 130. As can be seen from FIG. 7, there is a notable difference between the internal effort data 700 and the historical internal effort data 704, and also between the external work data 702 and the historical external work data 706.

Figure 8:
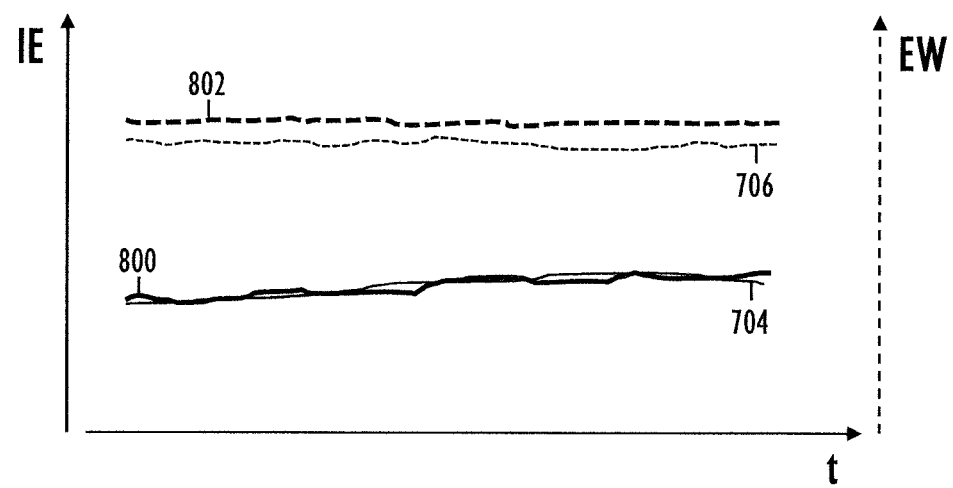

FIG. 8 illustrates an alternate example embodiment, wherein the comparison 118 indicates that the specific music track 116 is performance enhancing provided that, as compared to the historical internal effort data 704 and the historical external work data 706, the internal effort data 800 indicates an equal measured bodily input of the user 130, but the external work data 802 indicates a higher measured output effect of the user 130. As can be seen from FIG. 8, there is not a significant difference between the historical internal effort data 704 and the internal effort data 800.

Figure 9:
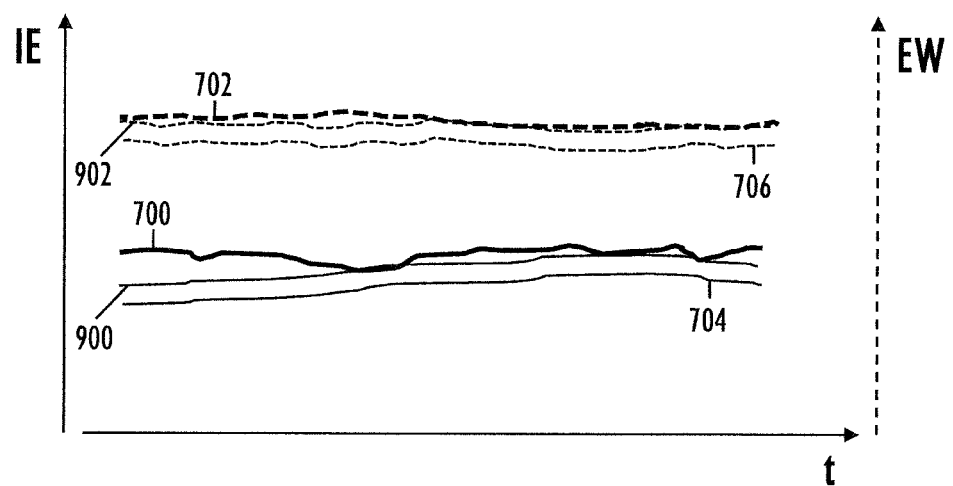

FIG. 9 illustrates a further example embodiment, wherein, for the comparison 118, the internal effort data, the historical external work data, the historical internal effort data and the historical external work data are calibrated in view of a physiological status of the user 130 during the measurement. Let us suppose that the non-calibrated data is shown in FIG. 7. Now, in FIG. 9, the internal effort data 700 and the external work data 702 remain the same, but the calibration has moved both the historical internal effort data 704 and the historical external work data 706 to a higher level, the calibrated values being shown with reference numerals 900 and 902. A typical scenario, illustrated by the FIG. 9 may be, for example: the physiological status of the user 130 during the latter measurement was "normal", whereby no calibration was necessary, whereas the physiological status of the user 130 during the earlier measurement indicated a "down" condition, meaning that his/her performance was poorer than in the normal condition. As a result of this processing, the historical data 900, 902 was calibrated to a higher level so that the new and the older data are comparable with each other. In a way, the day-to-day variation may be removed with the calibration.

In an example embodiment, the physiological status of the user 130 is determined based on at least one of data relating to the exercise session, data relating to a health status of the user 130, data relating to an overtraining status of the user 130. For example: the data relating to the exercise session may include data about the exercise frequency and exertion level, the data relating to the health status may indicate whether the user 130 is healthy, sick or convalescent, and the data relating to the overtraining status may indicate whether the user has exercised within his/her recovery capacity or whether the user has exceeded the recovery capacity.

Figure 10:
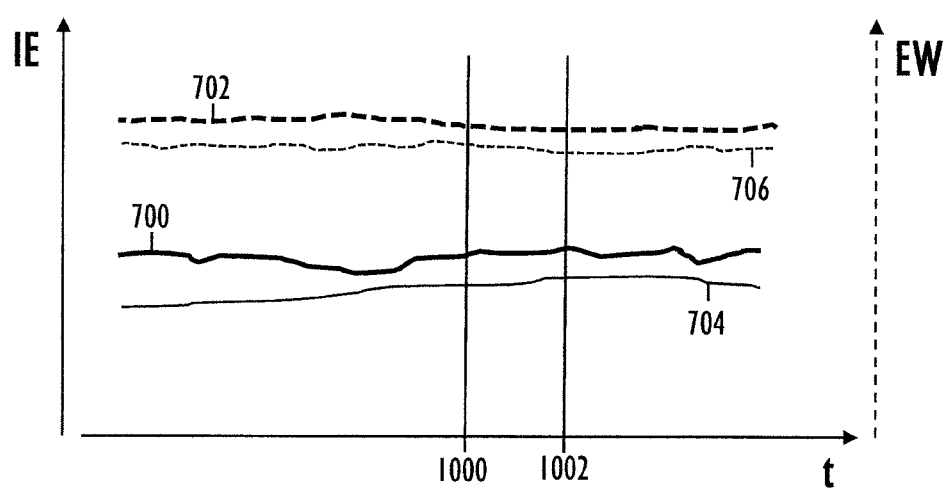

FIG. 10 illustrates another example embodiment, wherein a standard condition 1000-1002 is detected in the internal effort data 700 and the external work data 702, and the standard condition 1000-1002 is also detected in the historical internal effort data 704 and the historical external work data 706, whereupon the comparison 118 utilizes the internal effort data 700, the external work data 702, the historical internal effort data 704 and the historical external work data 706 measured during the standard condition 1000-1002. The standard condition may relate to an elapsed time of exercise, for example. In the example embodiment of FIG. 10, the standard condition is a time range beginning at time 1000 after the start of the exercise and ending at time 1002. The time range may be any suitable time range such as 1 minute, 2 minutes, 3 minutes, 5 minutes, 10 minutes etc. The standard condition may, additionally, or instead of, relate to a detected condition in the internal effort data 112 and/or external work data 114. For example, the detected condition may be such that a heart rate of the user 130 (featured in the internal effort data 112) needs to reach a certain level.

Note that FIGS. 7, 8, 9 and 10 illustrate just one example embodiment of the structure of the internal effort data 112 and external work data 114: the data 112, 114 may comprise a plurality of values as a function of time, or, alternatively/additionally, the data 112, 114 may comprise single values, data sets, statistical values, formulas, or values that characterize a total amount, an average amount or a representative amount of internal effort/external work. The comparison 118 operation may utilize various mathematical operations but also various methods for data analysis (including statistical analysis). An algorithm may identify a relationship (such as a correlation) between the internal effort data 112 and the external work data 114 caused by the specific music track 116.

Figure 2:
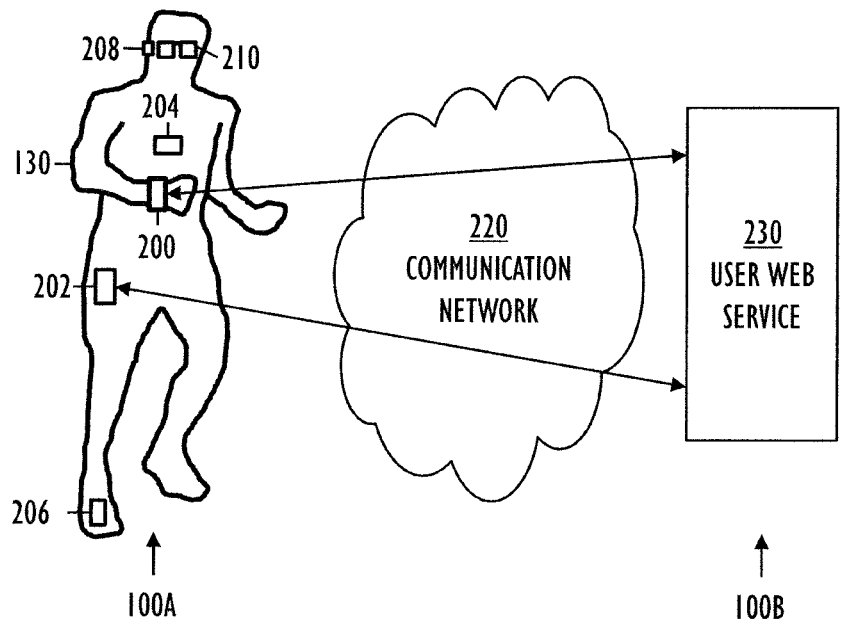

FIG. 2 illustrates an example embodiment wherein the electronic apparatus 100 is a part of configuration comprising various parts, designed and manufactured by the Applicant, Polar Electro Oy. As shown, the electronic apparatus 100 may be a user apparatus 100A handled by the user 130, and/or a server apparatus 1006 such as a user web service 230 providing service to the user 130.

The user 130 may be provided with a user apparatus 100A, which may be a single apparatus or a set of separate apparatuses, possibly being wearable and/or portable. With the user apparatus 100A, the user 130 may monitor training parameters that characterize the physiological state during the exercise in real-time. The physiological state may be detected from one or more performance metrics, such as by monitoring how the heart rate changes as the exercise session progresses.

The user apparatus 100A may comprise a wrist-worn apparatus 200 such as a sports watch or a smartwatch.

Furthermore, the user 130 may be provided with a heart rate transmitter 204 strapped around the chest, and possibly also with a shoe-mounted stride sensor 206. The user 130 may also carry a wireless headset 208, and/or smartglasses 210. The accessories 204, 206, 208, 210 may communicate wirelessly with the wrist-worn apparatus 200.

Additionally, or alternatively, the user apparatus 100A may comprise a portable communication apparatus 202 of the user 130. A non-exhaustive list of the types of the portable communication apparatus 202 includes: a mobile phone, a smartphone, a tablet computer, a phablet, a general-purpose mobile computing device. In an example embodiment, the portable communication apparatus 202 is a general-purpose off-the-shelf computing device, as opposed to a purpose-build proprietary equipment, whereby research & development costs will be lower as only the special-purpose software (and not the hardware) needs to be designed, implemented and tested. The portable communication apparatus 202 may employ a suitable operating system such as iOS, Android, or Windows Phone, for example.

Various accessories may be flexibly used as needed, i.e. all of them are not necessarily needed all the time, or by all users 130, or in all use cases.

However, in an example embodiment, the user apparatus 100A may also be interpreted as a circuitry implementing the required functionality within some suitable equipment.

The user apparatus 100A may store the exercise data, which the user (exerciser) 130 may use in post-analysis of the performed exercise. In an example embodiment, the post-analysis is processed in the user apparatus 100A.

In another embodiment, the exercise data is transferred from the user apparatus 100A to a user web service 230 through a communication network 220, and the post-analysis is carried out in the user web service 230.

If the wrist-worn apparatus 200 does not have a direct Internet access capability, the wrist-worn apparatus 200 may access the Internet (e.g. the user web service 230) via the portable communication apparatus 202 coupled to the wrist-worn apparatus 200, via a Bluetooth connection, for example. The portable communication apparatus 202 may be associated to the same user 130 as the wrist-worn apparatus 200.

The user web service 230 may comprise exercise data user accounts (UA), each exercise data user account comprising exercise data associated with a specific user 130. As such, there may be different user accounts for different users. An example embodiment of such a user web service 230 may be a Polar Personal Trainer (PTT), Polar Flow or iFIT service which comprises a database for storing the plurality of user accounts. In an example embodiment, the user web service 230 may require that the user 130 first connects to the user web service 230 by applying a user name and a password, or other identification means. The training/exercise data in the user account may have been stored during or after the exercise. The user account may additionally store physiological data of the user 130 and user attributes obtained from the exerciser 130 and/or the exercise device, such as name, gender, age, weight, height, image, status, motto, fitness level, training schedule, maximum oxygen intake (VO2Max), maximum heart rate (HRMax), performance zones (heart rate zones, speed zones), aerobic and anaerobic thresholds etc. Note that the described embodiments relating to the selection of the performance enhancing music are tied to the user; the music chosen is not generic, but user specific. One implementation of this may be such that the user is identified by a user identifier (which may be globally unique, or unique within a chosen domain) in the apparatus 100, and the internal effort data 112, external work data 114, the specific music track 116 and the performance enhancing music track 122 are specific for the user 130 identified by the user identifier.

Figure 3:
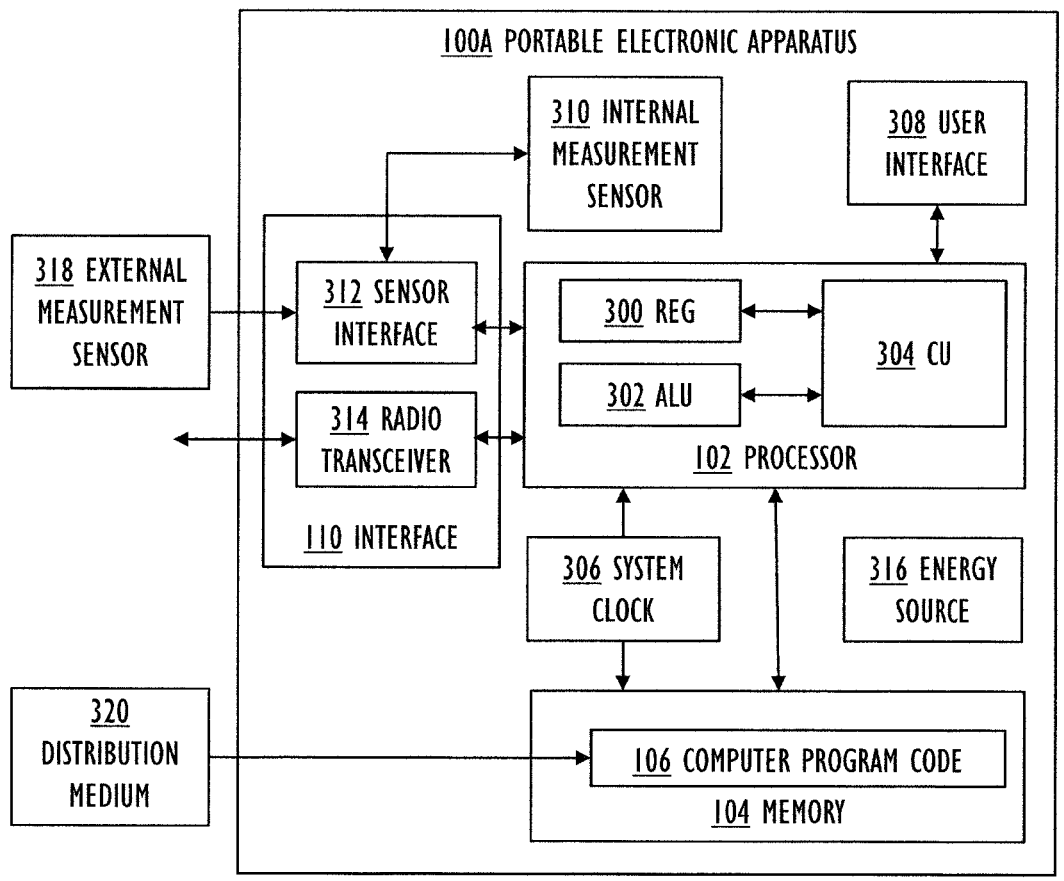
Figure 4:
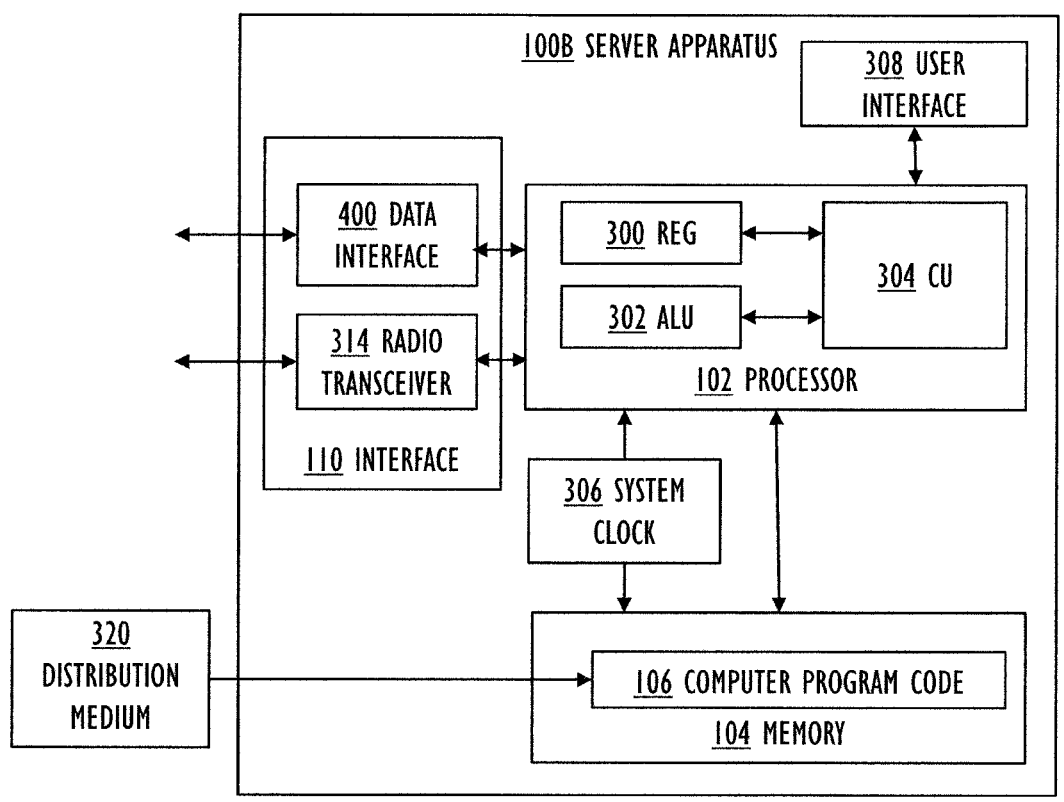

FIG. 3 illustrates example embodiments of the user apparatus 100A, whereas FIG. 4 illustrates example embodiments of the server apparatus 1006.

In an example embodiment, the server apparatus 100B may be implemented by a suitable computing resource or a combination of various computing resources.

In an example embodiment, the computing resource 100B may be implemented as a single server computer or as a cluster of computers. The server is a part of the client-server computing model that acts as distributed application which partitions tasks or workloads between the provider of a resource or service, called server, and the service requester, called client. The server 100B may serve a number of apparatuses 100A, 200, 202. The server computer 100B may be a host that is running one or more server programs which share their resources with clients 100A, 200, 202. The client 100A, 200, 202 may request a service function or content from the server 100B. Also, the client 100A, 200, 202 may initiate a communication session with the server 1006 which awaits incoming requests.

In an example embodiment, the electronic service 230/100B may also operate according to the cloud computing model, at least in part. Naturally, besides these example embodiments of the electronic service 230/100B, other feasible computing architectures may be utilized as well to implement the hardware and software of the electronic service 230/100B. Consequently, besides operating according to the client/server architecture, push technology may be utilized as well. In push technology, the request for a transaction is initiated by the electronic service 230/100B, whereas with the pull technology the request for the information is initiated by the client 100A, 200, 202.

The user apparatus 100A may comprise a user interface 308, the interface 110, the one or more processors 102, and the one or more memories 104 including the computer program code 106.

The user interface 308 implements exchange of graphical, textual and/or auditory information with the user 130. The user interface 308 may be realized with various techniques, such as the display, means for producing sound, a keyboard, and/or a keypad, for example. The means for producing sound may be a loudspeaker or a simpler means for producing beeps or other sound signals. The keyboard/keypad may comprise a complete (QWERTY) keyboard, a mere numeric keypad or only a few push buttons and/or rotary buttons. In addition, the user interface 308 may comprise other user interface components, for example various means for focusing a cursor (mouse, track ball, arrow keys, touch sensitive area etc.) or elements enabling audio control, or a fingerprint sensor enabling control with a fingerprint pattern of the users 130 finger(s).

The interface 110 of the user apparatus 100A may be implemented by a sensor interface 312 and/or a radio transceiver 314. The interface 110 of the server apparatus 1006 may be implemented by a data interface 400 (such as a network interface card) and/or a radio transceiver 314.

The sensor interface 312 may be utilized to obtain the internal effort data 112 and the external work data 114 measured relating to the user 130. The sensors may produce the data 112, 114 from users physical activity such as sports-, exercise-, or activity-related data.

In an example embodiment, the user apparatus 100A may further comprise one or more internal measurement sensors 310, and/or the apparatus 100A may be communicatively coupled with one or more external measurement sensors 318.

As illustrated in FIG. 3, the sensors 310, 318 may be internal measurement sensors 310 (within the apparatus 100A) and/or (wireless) external measurement sensors 318 (outside of the apparatus 100A). The apparatus 100A may comprise, as the sensor interface 312, a transceiver for communicating with the wireless external measurement sensor(s) 318, or even just a receiver for receiving measurements from the wireless external measurement sensors 318. For the internal measurement sensors 310, the interface 312 may be a suitable hardware communication interface such as a wired interface or an appropriate communication bus, for example.

The following is a non-limiting list of possible types of the physical activity data (also known as physiological sensor data or exercise data) that may be detected by the sensors 310, 318 or that the apparatus 100A may determine on the basis of the physical activity data: heart rate zones, heart rate samples, heart rate variation samples, heart beat interval samples, breathing activity, fat consumption rate, calorie/energy consumption rate, consumed amount of calories/energy, stress of the user, activity zones, activity samples, speed and/or pace samples, power samples, acceleration of the user, peak work output, economy of motion of the user, cadence samples, altitude samples, temperature samples, location samples, distance elapsed, time elapsed, pedal index, left-right balance, running index, training load, galvanic skin response samples, electrodermal activity status, fluid balance, skin temperature samples, heading samples and/or bike angles. The location data may comprise satellite positioning data, such as, GPS positioning data, or any other data that allows the determination of the location of the exerciser during the exercise at any given time. The movement indoors may be detected via indoor location tracking methods, such as mapping techniques including measuring Earth's magnetic fields or radio frequency signals.

A non-exhaustive list of sensors 310, 318 includes heart activity sensors, motion sensors, location sensors, swimming sensors and bike sensors, as well as other sensors gathering information regarding the exercise. Besides these, sensors 310, 318 may comprise any sensors that are needed for detecting a given exercise data type, such as temperature sensor for detecting ambient temperature or skin temperature.

The heart activity sensors may be configured to determine heart activity, such as heart rate, Heart Beat Interval (HBI) and/or Heart Rate Variability (HRV), for example. The heart activity sensors include, but are not limited to, a cardiovascular sensor (such as an electrocardiogram ECG sensor), an optical heart activity sensor such as a PPG (photoplethysmography) sensor, or a bioimpedance plethysmography. The optical heart activity sensor may detect the heart activity of the user by optical heart rate measurement, which may comprise sending a light beam towards skin of the user and measuring the bounced and/or emitted light from the skin of the user. The light beam may alter when travelling through veins of the user and the alterations may be detected by the optical heart rate activity sensor. Further, besides these types of heart activity sensors, also other types of biosignal measurement sensors may be embedded into the heart activity sensors. These types include but are not limited to the following: a Laser Doppler-based blood flow sensor, a magnetic blood flow sensor, an Electromechanical Film (EMFi) pulse sensor, a polarization blood flow sensor. In an example embodiment, the heart activity sensor may produce raw measurement data of the heart activity and/or it may process the measurement data into heart activity information, such as heart rate for example. This means that the sensor(s) 310, 318 in general may comprise data processing capabilities. Further, the raw measurement data and/or processed information may be processed by the apparatus 100A and/or transmitted to an external device, such as the portable communication apparatus 202, or even to the user web service 230, as was explained earlier.

Motion sensors may be configured to measure motion induced by the user 130 to the apparatus 100A by moving hand (or other body parts such as chest or ankle to which the motion sensor is attached to). The motion sensor may use other motion data, such as location data of the user, to determine motion of the user. In an example embodiment, the motion sensor comprises at least one of the following: an accelerometer, a magnetometer, and a gyroscope. The motion sensor may further comprise sensor fusion software for combining the accelerometer data and gyroscope data so as to provide physical quantities, such as acceleration data, velocity data, or limb trajectory data in a reference coordinate system having orientation defined by a predetermined gyroscope orientation.

Location sensors may utilize GPS (Global Positioning System) or other satellite-based, or radio system-based system for locating the user and measuring various parameters (speed, distance, location, route) relating to the movement of the user.

Swimming sensors may measure swimming specific parameters such as number of strokes or distance, for example.

Bike sensors may be sensors attached to various parts of the bike for measuring speed, cadence, or power, for example.

The gathered sensor information may be utilized to calculate further physical activity data of the user such as total energy consumption, an energy consumption speed, an activity level, a cumulated activity, for example.

Described physical activity data and sensor data may be used to generate the internal effort data 112 and the external work data 114.

The radio transceiver 314 may comprise a cellular radio transceiver and/or a non-cellular radio transceiver. In an example embodiment, the cellular radio transceiver 314 may be interoperable with various wireless standard/non-standard/proprietary cellular radio networks 220 such as any mobile phone network, which may be coupled with a wired network such as the Internet.

In an example embodiment, the wireless communication network 220 comprises any mobile phone network, regardless of the generation (such as 2G, 3G, 4G, beyond 4G, 5G etc.) such as GSM (Global System for Mobile Communications), GPRS (General Packet Radio Service), EGPRS (Enhanced GPRS), WCDMA (Wideband Code Division Multiple Access), UMTS (Universal Mobile Telephone System), 3GPP (The 3rd Generation Partnership Project), IMT (International Mobile Telecommunication), LTE (Long Term Evolution, LTE-A (LTE-Advanced), Mobile WiMAX, and other radio systems (in their present forms and/or in their evolution forms).

In an example embodiment, the communication network 220 supports the use of subscriber identity module (SIM), which may be an integrated circuit storing subscriber data, which is network-specific information used to authenticate and identify the subscriber on the cellular network. The subscriber identity module may be embedded into a removable SIM card. Consequently, the apparatus 100A may include the SIM card (and a SIM card reader). Alternatively, the apparatus 100A may include a virtual or software SIM card.

In an example embodiment, the wireless communication network 220 comprises a wireless local area network (WLAN), a hotspot, or an access point, all of which may provide Internet access through the use of a router connected to a link to an Internet service provider.

In an example embodiment, the non-cellular radio transceiver 314 may utilize a short-range wireless technology, a Bluetooth standard, a Bluetooth low energy (BLE) standard, a wireless local area network (WLAN) standard, a Wi-Fi (or WiFi) standard, a IEEE (Institute of Electrical and Electronics Engineers) 802.11 standard or its evolution versions (IEEE 802.11ac etc.), for example), a proprietary short-range radio technology.

In an example embodiment, a system clock 306 constantly generates a stream of electrical pulses, which cause the various transferring operations within the apparatus 100 to take place in an orderly manner and with specific timing.

In an example embodiment, the processor 102 may be implemented as a microprocessor implementing functions of a central processing unit (CPU) on an integrated circuit. The CPU is a logic machine executing a computer program code 106. The computer program code 106 may be coded as a computer program using a programming language, which may be a high-level programming language, such as C, or Java, or a low-level programming language, such as a machine language, or an assembler. The CPU may comprise a set of registers 300, an arithmetic logic unit (ALU) 302, and a control unit (CU) 304. The control unit 304 is controlled by a sequence of the computer program code 106 transferred to the CPU from the (working) memory 104. The control unit 304 may contain a number of microinstructions for basic operations. The implementation of the microinstructions may vary, depending on the CPU design. The microprocessor 102 may also have an operating system (a dedicated operating system of an embedded system, a real-time operating system, or even a general-purpose operating system), which may provide the computer program code 106 with system services.

A non-exhaustive list of implementation techniques for the processor 102 and the memory 104 includes, but is not limited to: logic components, standard integrated circuits, application-specific integrated circuits (ASIC), system-on-a-chip (SoC), application-specific standard products (ASSP), microprocessors, microcontrollers, digital signal processors, special-purpose computer chips, field-programmable gate arrays (FPGA), and other suitable electronics structures.

In an example embodiment, the processor 102 and the memory 104 of the apparatus 100 are a part of a microcontroller. In an example embodiment, the sensor interface 312, and/or the radio transceiver 314 also belong to the microcontroller.

In an example embodiment, the sensor interface 312, the radio transceiver 314, the processor 102 and the memory 104 are separate entities, communicatively coupled together by an appropriate serial bus, for example. In general interfaces between the various elements may be implemented with suitable interface technologies, such as a message interface, a method interface, a sub-routine call interface, a block interface, an appropriate serial/parallel bus, or any hardware/software means enabling communication between various sub-units of the apparatus 100.

An example embodiment provides a computer-readable medium 320 for the apparatus 100 comprising a computer program comprising the computer program code 106. Said computer program code 106, when loaded into the apparatus 100 and executed in the apparatus 100, causes the apparatus 100 to perform the operations required to implement the described example embodiments. In an example embodiment, the computer program code 106 may be in source code form, object code form, executable file, or in some intermediate form. The computer-readable medium 320 may comprise at least the following: any entity or device capable of carrying computer program code 106 to the apparatus 100, a record medium, a computer memory, a read-only memory, an electrical carrier signal, a telecommunications signal, and a software distribution medium. In some jurisdictions, depending on the legislation and the patent practice, the computer-readable medium 320 may not be the telecommunications signal. In an example embodiment, the computer-readable medium 320 may be a non-transitory computer readable storage medium.

In an example embodiment, the apparatus 100A may further comprise an independent energy source 316. In an example embodiment, the energy source 316 may be an electric battery converting stored chemical energy into electrical energy. The electric battery 316 may be rechargeable. In an example embodiment, the apparatus 316 may comprise a power interface to receive electrical energy for charging the battery 316. The power interface may couple the apparatus 100A to mains electricity, to a charger connector in a vehicle, or to some other power source enabling the charging of the battery 316. In addition to, or instead of, the battery 316, the apparatus 100 may comprise another portable energy source such as a solar cell 316 converting the energy of light directly into electricity by the photovoltaic effect, or a a fuel cell 316 converting the chemical energy from a fuel into electricity through a chemical reaction with oxygen or another oxidizing agent.

Figure 5:
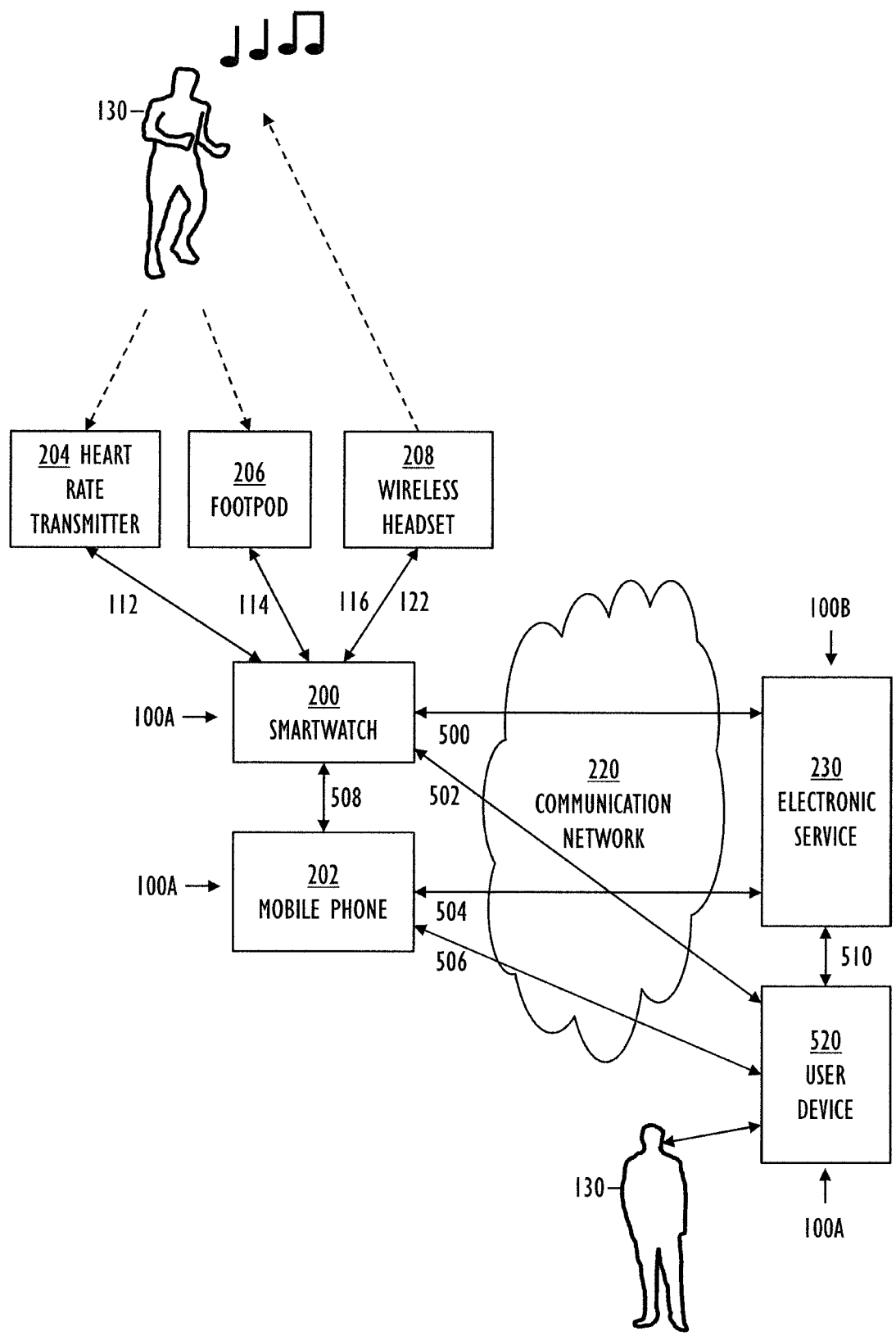

FIG. 5 illustrates the operation environment of FIG. 2 from a slightly different perspective. The apparatus 100 functionality may be implemented in one specific component, or distributed among a number of different components: into the user apparatus 100A such as the smartwatch 200, mobile phone 202 and/or a computing device 520, and/or into the server apparatus 100B such as the electronic service 230. Besides these, the apparatus 100 functionality may be implemented in another device, such as in the wireless headset 208. As shown, the apparatuses 100A, 100B may communicate 500, 502, 504, 506, 508, 510 with each other.

Figure 6:
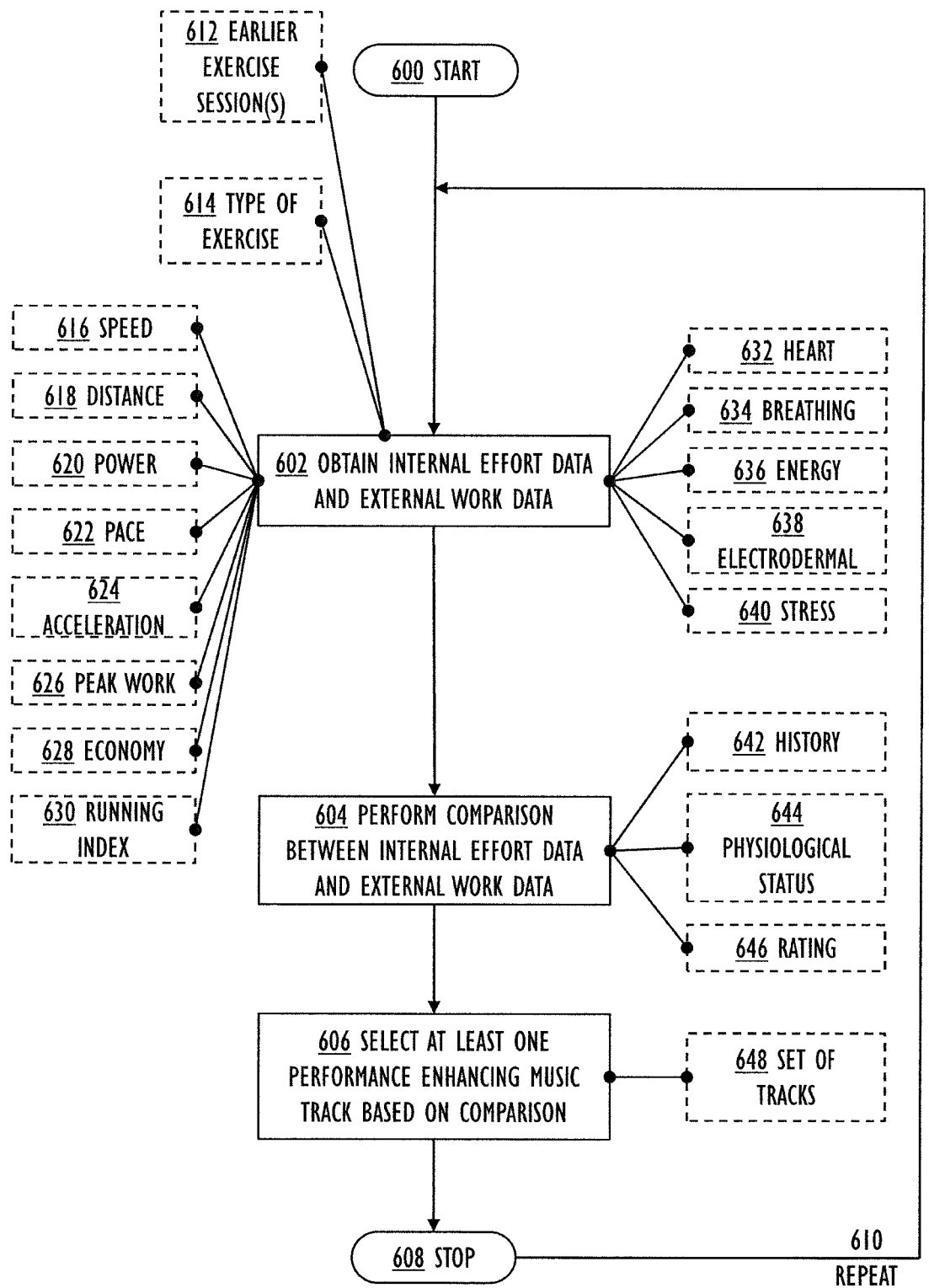
FIG. 6 is a flow-chart illustrating further example embodiments.

Next, let us study FIG. 6, which is a flow chart illustrating further example embodiments. The operations are not strictly in chronological order, and some of the operations may be performed simultaneously or in an order differing from the given ones. Other functions may also be executed between the operations or within the operations and other data exchanged between the operations. Some of the operations or part of the operations may also be left out or replaced by a corresponding operation or part of the operation. It should be noted that no special order of operations is required, except where necessary due to the logical requirements for the processing order. In an example embodiment, the method illustrated in FIG. 6 may be implemented by an electronic apparatus. In an example embodiment, the method may be implemented by the described electronic apparatus 100/100A/100B.

The method starts in 600.

In 602, internal effort data and external work data both measured from a user performing an exercise while listening to a specific music track are obtained. The internal effort data describes a measured bodily input of the user, and the external work data describes a measured output effect of the user.

In 604, a comparison between the internal effort data and the external work data is performed.

In 606, at least one performance enhancing music track for the user is selected based on the comparison.

The method ends in 608, or, alternatively, the operations 602-604-606 and the supplementary operations may be repeated 610 as required.

The already described example embodiments of the apparatus 100/100A/100B may be utilized to enhance the method with various further example embodiments.

Next, let us study further example embodiments of the method and the apparatus 100/100A/100B with reference to FIG. 6.

In an example embodiment, the internal effort data 112 comprises at least one of a heart activity 632 of the user, a breathing activity 634 of the user, an energy consumption 636 of the user, an electrodermal activity status 638 of the user, a stress 640 of the user.

In an example embodiment, the external work data 114 comprises at least one of a speed 616 of the user, a distance 618 traveled by the user, a power 620 outputted by the user, a pace 622 of the user, an acceleration 624 of the user, a peak work output 626 by the user, an economy of motion status 628 of the user, a running index 630 of the user.

In an example embodiment, historical internal effort data 642 and historical external work data 642 from at least one earlier exercise session 612 by the user are taken into account in the comparison 604.

In an example embodiment, for the comparison 604, the internal effort data, the historical external work data, the historical internal effort data and the historical external work data are calibrated in view of a physiological status 644 of the user during the measurement.

In an example embodiment, a playback of the specific music track 116 is repeated consecutively during the exercise, and the internal effort data 112 and external work data 114 are both measured from the user 130 performing the exercise while listening to the consecutively repeated specific music track 116. With this example embodiment, the effect of the specific music track 116 may become more apparent.

In an example embodiment, a playback of the specific music track 116 is repeated consecutively during more than one separate exercise session, and the internal effort data 112 and external work data 114 are both measured from the user performing the exercise in the more than one separate exercise sessions while listening to the specific music track 116. This example embodiment may also clarify the effect of the specific music track 116 as multiple measurement results are obtained and compared.

In an example embodiment, the specific music track 116 is added to a set 648 of performance enhancing music tracks, if the comparison 604 indicates that the specific music track is performance enhancing.

In an example embodiment, at least one music track similar to the specific music track 116 is added to a set 648 of performance enhancing music tracks, if the comparison 604 indicates that the specific music track 116 is performance enhancing. Each music track may have a number of different parameters, with which music tracks may be classified, grouped or tagged. The parameters may define one or more of the following features: a rhythm (beat or tempo) of the music track 116, 122, a dynamic range of the music track 116, 122, an audio spectrum of the music track 116, 122, a genre of the music track 116, 122, musicality (harmony, melody) of the music track 116, 122, cultural impact of the music track 116, 122, and association of the music track 116, 122.

In an example embodiment, a performance rating 646 is assigned for the specific music track 116 based on the comparison 604. The performance rating 646 may be a Boolean value (performance enhancing/not performance enhancing) or a scale (for example: 1=very performance enhancing, 2=performance enhancing, 3=no effect). In an example embodiment, in order to assign the performance rating 646 for the specific music track 116, besides the comparison 604, also at least one performance rating for the specific music track 116 originating from at least one earlier exercise session is taken into account. In this way, the performance rating becomes more accurate.

In an example embodiment, a type 614 of the exercise is detected, and the specific music track 116 is associated with the type of the exercise. In an example embodiment, a specific type of the internal effort data 112 and a specific type of the external work data 114 are selected based on the type 614 of the exercise and used in the comparison 604. The type of the exercise may refer to the sport, such as running, bicycling, skiing etc. or to the structure/effect of the exercise, such as interval, long slow distance etc. Music may be played during all types of training sessions: free sessions with self-selected pace, long endurance sessions, high intensity interval sessions, strength training sessions, and the physiological effects of each music track is analyzed in this context. In an example embodiment, the type of the exercise refers to a predetermined heart rate range. The heart range may be determined by a range related to the maximum heart rate of the user. Polar Sport Zones, for example determined the following ranges: maximum—90-100% of the maximum heart rate, hard—80-90% of the maximum heart rate, moderate—70-80% of the maximum heart rate, light—60-70% of the maximum heart rate, and very light—50-60% of the maximum heart rate.

In an example embodiment, the specific music track 116 has been selected for the listening based on the type of the exercise 614. In this way, the music may be better suited to the nature of the type. For example: interval training may require faster beat, whereas long slow distance is better served with moderate beat.

It will be obvious to a person skilled in the art that, as technology advances, the inventive concept can be implemented in various ways. The invention and its embodiments are not limited to the example embodiments described above but may vary within the scope of the claims.

What is claimed is:

1. A wrist-worn electronic apparatus comprising:
a wireless interface;
an optical heart activity sensor;
a location sensor;
a music player;
one or more processors; and
one or more memories including computer program code,
the one or more memories and the computer program code configured to, with the one or more processors, cause the apparatus to perform operations comprising:
obtaining, internal effort data from an optical heart activity sensor and external work data from a location sensor both measured from a user performing an exercise while listening to a specific music track played with the music player and outputted through the wireless interface to one of a loudspeaker, headphones, wireless headset, earbuds, the internal effort data describing a measured bodily input of the user, and the external work data describing a measured output effect of the user;
performing a comparison between the internal effort data and the external work data, wherein the comparison detects that the specific music track is performance enhancing if a relationship indicating an improved economy of locomotion during submaximal effort between the internal effort data and the external work is identified, wherein the comparison takes historical internal effort data and historical external work data from at least one earlier exercise session by the user into account; and adding the specific music track to a set of performance enhancing music tracks if the comparison detects that the specific music track is performance enhancing.

2. The apparatus of claim 1, wherein the comparison indicates that the specific music track is performance enhancing provided that, as compared to the historical internal effort data and the historical external work data, the internal effort data indicates an increase in the measured bodily input of the user and the external work data indicates an increase in the measured output effect of the user.

3. The apparatus of claim 1, wherein the comparison indicates that the specific music track is performance enhancing provided that, as compared to the historical internal effort data and the historical external work data, the internal effort data indicates an equal measured bodily input of the user, but the external work data indicates a higher measured output effect of the user.

4. The apparatus of claim 1, wherein, for the comparison, the internal effort data, the historical external work data, the historical internal effort data and the historical external work data are calibrated in view of a physiological status of the user during the measurement.

5. The apparatus of claim 4, wherein the physiological status is determined based on at least one of data relating to the exercise session, data relating to a health status of the user, data relating to an overtraining status of the user.

6. The apparatus of claim 1, wherein a playback of the specific music track is repeated consecutively during the exercise, and the internal effort data and external work data are both measured from the user performing the exercise while listening to the consecutively repeated specific music track.

7. The apparatus of claim 1, wherein a playback of the specific music track is repeated consecutively during more than one separate exercise session, and the internal effort data and external work data are both measured from the user performing the exercise in the more than one separate exercise sessions while listening to the specific music track.

8. The apparatus of claim 1, wherein at least one music track similar to the specific music track is added to a set of performance enhancing music tracks, if the comparison indicates that the specific music track is performance enhancing.

9. The apparatus of claim 1, wherein a performance rating is assigned for the specific music track based on the comparison.

10. The apparatus of claim 9, wherein, in order to assign the performance rating for the specific music track, besides the comparison, also at least one performance rating for the specific music track originating from at least one earlier exercise session is taken into account.

11. The apparatus of claim 1, wherein a type of the exercise is detected, and the specific music track is associated with the type of the exercise.

12. The apparatus of claim 11, wherein a specific type of the internal effort data and a specific type of the external work data are selected based on the type of the exercise and used in the comparison.

13. The apparatus of claim 11, wherein the specific music track has been selected for the listening based on the type of the exercise.

14. The apparatus of claim 1, wherein the internal effort data comprises at least one of a heart activity of the user, a breathing activity of the user, an energy consumption of the user, an electrodermal activity status of the user, a stress of the user.

15. The apparatus of claim 1, wherein the external work data comprises at least one of a speed of the user, a distance traveled by the user, a power outputted by the user, a pace of the user, an acceleration of the user, a peak work output by the user, an economy of motion status of the user, a running index of the user.

16. The apparatus of claim 1, wherein the internal effort data comprises a heart rate of the user, and the external work data comprises at least one of a speed of the user, a distance traveled by the user, a pace of the user, an economy of motion status of the user, a running index of the user.

17. The apparatus of claim 1, wherein a standard condition is detected in the internal effort data and the external work data, and the standard condition is also detected in the historical internal effort data and the historical external work data, whereupon the comparison utilizes the internal effort data, the external work data, the historical internal effort data and the historical external work data measured during the standard condition.

18. A non-transitory computer-readable storage medium comprising a computer program comprising computer program code which, when executed by an electronic apparatus causes the apparatus to perform operations comprising:
obtaining, internal effort data from an optical heart activity sensor and external work data from a location sensor both measured from a user performing an exercise while listening to a specific music track, the internal effort data describing a measured bodily input of the user, and the external work data describing a measured output effect of the user;
performing a comparison between the internal effort data and the external work data, wherein the comparison detects that the specific music track is performance enhancing if a relationship indicating an improved economy of locomotion during submaximal effort between the internal effort data and the external work is identified, wherein the comparison takes historical internal effort data and historical external work data from at least one earlier exercise session by the user into account; and
adding the specific music track to a set of performance enhancing music tracks if the comparison detects that the specific music track is performance enhancing.

19. A method in an electronic apparatus, comprising:
obtaining internal effort data from an optical heart activity sensor and external work data from a location sensor both measured from a user performing an exercise while listening to a specific music track, the internal effort data describing a measured bodily input of the user, and the external work data describing a measured output effect of the user;
performing a comparison between the internal effort data and the external work data, wherein the comparison detects that the specific music track is performance enhancing if a relationship indicating an improved economy of locomotion during submaximal effort between the internal effort data and the external work is identified, wherein the comparison takes historical internal effort data and historical external work data from at least one earlier exercise session by the user into account; and
adding the specific music track to a set of performance enhancing music tracks if the comparison detects that the specific music track is performance enhancing.

* * * * *